United States Patent
Levorse, Jr. et al.

(10) Patent No.: US 7,304,028 B2
(45) Date of Patent: Dec. 4, 2007

(54) USE OF METHYL BENZOIC ACID ESTER IN PERFUME COMPOSITIONS

(75) Inventors: Anthony T. Levorse, Jr., Westfield, NJ (US); Richard Anthony Weiss, Livingston, NJ (US); Manfred Pawlak, Princeton, NJ (US)

(73) Assignee: International Flavors & Fragrances Inc., NY, NY (US)

( * ) Notice: Subject to any disclaimer, the term of this patent is extended or adjusted under 35 U.S.C. 154(b) by 762 days.

(21) Appl. No.: 10/768,730

(22) Filed: Jan. 29, 2004

(65) Prior Publication Data

US 2005/0170998 A1 Aug. 4, 2005

(51) Int. Cl.
*A61K 8/00* (2006.01)
*C07C 15/04* (2006.01)

(52) U.S. Cl. .............................. 512/26; 512/25; 512/8; 568/308; 568/335

(58) Field of Classification Search .................... 512/8, 512/2, 25, 26; 604/290; 568/308, 335
See application file for complete search history.

(56) References Cited

U.S. PATENT DOCUMENTS

| | | | |
|---|---|---|---|
| 3,745,173 A | | 7/1973 | Henry |
| 4,808,569 A | * | 2/1989 | Chaudhuri et al. ............. 512/2 |
| 5,559,088 A | | 9/1996 | Severns et al. |
| 5,750,125 A | | 5/1998 | Lahanas et al. |
| 6,086,903 A | | 7/2000 | Trinh et al. |
| 6,680,289 B1 | | 1/2004 | Woo et al. |
| 2003/0009138 A1 | * | 1/2003 | Freeman et al. ............. 604/290 |
| 2003/0166499 A1 | | 9/2003 | Yang et al. |

OTHER PUBLICATIONS

Imai, Toshihiro, et al., Attractiveness of methyl anthranilate and its related compounds to the flower thrips, (Thrips hawaiiensis (Morgan), T. coloratus Schmutz and Megalurothrips distalis (Karny)(Thysanoptera: Thripidae), Aug. 8, 2001, Applied Entomolgical Zoology, 36 (4): 475-478.*

* cited by examiner

*Primary Examiner*—Walter D. Griffin
*Assistant Examiner*—Christine T Mui
(74) *Attorney, Agent, or Firm*—Elizabeth M. Quirk; Joseph F. Leightner

(57) ABSTRACT

The use of 2-methyl-benzoic acid methyl ester as a fragrance chemical, suitable for use in creating fragrance, and scents in items such as perfumes, colognes and personal care products is disclosed.

7 Claims, No Drawings

USE OF METHYL BENZOIC ACID ESTER IN PERFUME COMPOSITIONS

FIELD OF THE INVENTION

The use of 2-methyl-benzoic acid methyl ester is disclosed as a fragrance chemical suitable for incorporation in fine fragrances, cosmetics, toiletries and related applications.

BACKGROUND OF THE INVENTION

There is an ongoing need in the fragrance industry to provide new chemicals to give perfumers and other formulation experts ability to create new fragrances for perfumes, colognes and personal care products.

The preparation of 2-methyl-benzoic acid methyl ester is disclosed by Raikow; Tischkow; CZCAA % ; Chem-Ztg. Chem. Appar.; 29; 1905; 1269 and Kellas; ZEPPCAC; Z. Phys. Chem. Stoechiom. Verwandtschaftsl.; 24; 1897; 221. One route for preparing the compound is by reacting 2-methyl benzoic acid with methanol in the presence of a strong acid, such as sulfuric acid.

Despite the above disclosure of 2-methyl-benzoic acid methyl ester, the literature fails to disclose or suggest the use of 2-methyl-benzoic acid methyl ester as a fragrance chemical.

SUMMARY OF THE INVENTION

The present invention is directed to the use of 2-methyl-benzoic acid methyl ester as a fragrance chemical to enhance fragrance in perfumes, toilet waters, colognes, personal products and the like. More specifically, the present invention is a method for enhancing a perfume by incorporating an olfactory acceptable amount of compound of the formula:

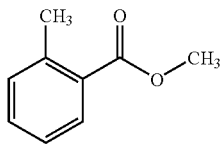

These and other embodiments of the present invention will be apparent by reading the following specification.

DETAILED DESCRIPTION OF THE INVENTION

We have discovered that 2-methyl-benzoic acid methyl ester has fragrance notes of ylang, orange flower, and grape that is well suited for use as a fragrance chemical.

The use of this compound is widely applicable in current perfumery products, including the preparation of perfumes and colognes, the perfuming of personal care products such as soaps, shower gels, and hair care products as well as air fresheners, candles and cosmetic products. The compound can also be used to perfume candles and cleaning agents, such as, but not limited to soaps, detergents, dishwashing materials, scrubbing compositions, window cleaners, and the like.

As described herein, the present invention is well suited for use in a variety of well-known consumer products such as laundry detergent and fabric softeners, liquid dish detergents, automatic dish detergents, as well as hair shampoos and conditioners. These products employ surfactant and emulsifying systems that are well known. For example, fabric softener systems are described in U.S. Pat. Nos. 6,335,315, 5,674,832, 5,759,990, 5,877,145, 5,574,179; 5,562,849, 5,545,350, 5,545,340, 5,411,671, 5,403,499, 5,288,417, 4,767,547 and 4,424,134. Liquid dish detergents are described in U.S. Pat. Nos. 6,069,122 and 5,990,065 ; and automatic dish detergent products are described in U.S. Pat. Nos. 6,020,294, 6,017,871, 5,968,881, 5,962,386, 5,939,373, 5,914,307, 5,902,781, 5,705,464, 5,703,034, 5,703,030, 5,679,630, 5,597,936, 5,581,005, 5,559,261, 4,515,705, 5,169,552, and 4,714,562. Liquid laundry detergents which can use the present invention include those systems described in U.S. Pat. Nos. 5,929,022, 5,916,862, 5,731,278, 5,565,145, 5,470,507, 5,466,802, 5,460,752, 5,458,810, 5,458,809, 5,288,431, 5,194,639, 4,968,451, 4,597,898, 4,561,998, 4,550,862, 4,537,707, 4,537,706, 4,515,705, 4,446,042, and 4,318,818. Shampoos and conditioners that can employ the present invention include U.S. Pat. Nos. 6,162,423, 5,968,286, 5,935,561, 5,932,203, 5,837,661, 5,776,443, 5,756,436, 5,661,118, 5,618,523, 5,275,755, 5,085,857, 4,673,568, 4,387,090, and 4,705,681.

In these preparations, the compound of the present invention can be used alone or in combination with other fragrance compositions, solvents, adjuvants and the like. Those with skill in the art will appreciate the nature and variety of the other ingredients that can be used in combination with the compound of the present invention.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, and carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. Nos. 4,534,891, 5,559,088, 6,086,903, and 6,680,289. Another source of suitable fragrances is found in *Perfumes, Cosmetics and Soaps*, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

As used herein olfactory effective amount is understood to mean the amount of compound in perfume compositions the individual component will contribute to its particular olfactory characteristics, but the olfactory effect of the perfume composition will be the sum of the effects of each of the perfume or fragrance ingredients. Thus the compound of the invention can be used to alter the aroma characteristics of the perfume composition by modifying the olfactory reaction contributed by another ingredient in the composition. The amount will vary depending on many factors including other ingredients, their relative amounts and the effect that is desired.

The level of compound of the invention employed in the perfumed article varies from about 0.005 to about 10 weight percent, preferably from about 0.1 to about 8 and most preferably from about 0.5 to about 5 weight percent. In addition to the compound, other agents can be used in conjunction with the fragrance. Well known materials such as surfactants, emulsifiers, and polymers to encapsulate the fragrance can also be employed without departing from the scope of the present invention.

Another method of reporting the level of the compound of the invention in the perfumed composition, i.e., the compound as a weight percentage of the materials added to impart the desired fragrance. The compound of the invention can range widely from 0.005 to about 10 weight percent of the perfumed composition, and preferably from about 0.1 to about 5 weight percent. Those with skill in the art will be able to employ the desired level of the compound of the invention to provide the desired fragrance and intensity.

The following are provided as specific embodiments of the present invention. Other modifications of this invention will be readily apparent to those skilled in the art, without departing from the scope of this invention. As used herein all percentages are weight percent. The materials used in the following example were obtained from International Flavors & Fragrances Inc., DPG is understood to mean dipropylene glycol and DEP is understood to mean diethylphthalate. All U.S. Patents and Published patent applications are hereby incorporated by reference as if set forth in their entirety.

EXAMPLE 1

Incorporation of 2-methyl-benzoic acid methyl ester in a grape fragrance formulation:

|  | + | − |
|---|---|---|
| Citronellyl Acetate | 1.50 | 1.50 |
| Dipropylene Glycol | 15.50 | 15.50 |
| Ethyl Acetate 98/99 Undenatured | 1.00 | 1.00 |
| Ethyl Aceto Acetate | 0.50 | 0.50 |
| Ethyl Butyrate | 4.00 | 4.00 |
| Ethyl Propionate | 40.00 | 40.00 |
| Ethyl Valerate | 0.50 | 0.50 |
| Ethyl Vanillin | 1.50 | 1.50 |
| Methyl Anthranilate | — | 3.00 |
| Oenanthic Ether | 0.50 | 0.50 |
| Palatone 2% DPG | 25.00 | 25.00 |
| Phenyl Ethyl Isobutyrate | 0.50 | 0.50 |

-continued

|  | + | − |
|---|---|---|
| Pineapple Compound 15% DEP | 7.50 | 7.50 |
| Styralyl Acetate | 0.50 | 0.50 |
| Vanillin Ex Lignin | 1.50 | 1.50 |
| 2-methyl benzoic acid methyl ester | 3.00 | — |

The 2-methyl-benzoic acid methyl ester compares favorable with methyl anthranilate in fragrances. The above formulation was described as having a grape character and enhancing the overall strength of the formulation through the incorporation of the 2-methyl-benzoic acid methyl ester. The above fragrance formulations were presented to demonstrate the effectiveness of the compound of the present invention in enhancing, improving or modifying the performance of the formulations in which they are incorporated.

What is claimed is:

1. A method for improving, enhancing or modifying a fragrance through the addition of an olfactory acceptable amount of 2-methyl-benzoic acid methyl ester.

2. The method of claim 1, wherein the fragrance is incorporated into a product selected from perfumes, colognes, candles, toilet waters, cosmetic products, personal care products, fabric care products, cleaning products and air fresheners.

3. The method of claim 2, wherein the cleaning product is selected from the group consisting of soaps, detergents, dishwashing compositions, scrubbing compounds and window cleaners.

4. The method of claim 2, wherein the product is a personal care product.

5. The method of claim 1, wherein the amount is from about 0.005 to about 10 weight percent.

6. The method of claim 1, wherein the amount is from about 0.1 to about 8 weight percent.

7. The method of claim 1, wherein the amount is from about 0.5 to about 5 weight percent.

* * * * *